United States Patent [19]

Exconde

[11] Patent Number: 5,658,307
[45] Date of Patent: Aug. 19, 1997

[54] METHOD OF USING A SURGICAL DISSECTOR INSTRUMENT

[76] Inventor: Primo D. Exconde, 450 N. Pickaway St., Circleville, Ohio 43113

[21] Appl. No.: 603,012

[22] Filed: Feb. 16, 1996

Related U.S. Application Data

[63] Continuation of Ser. No. 168,990, Dec. 17, 1993, abandoned, which is a continuation-in-part of Ser. No. 927,552, Aug. 6, 1992, abandoned, which is a continuation of Ser. No. 610,119, Nov. 7, 1990, abandoned.

[51] Int. Cl.⁶ .................................................. A61B 17/00
[52] U.S. Cl. .......................................................... 606/190
[58] Field of Search .................................. 128/898, 757, 128/758; 606/190, 170, 180, 85; 604/22

[56] References Cited

U.S. PATENT DOCUMENTS

| | | | |
|---|---|---|---|
| 3,618,611 | 11/1971 | Urban | 606/170 |
| 3,937,222 | 2/1976 | Banko | 606/170 |
| 3,976,077 | 8/1976 | Kirfoot . | |
| 4,646,738 | 3/1987 | Trott | 606/170 |
| 4,705,038 | 11/1987 | Sjostrom et al. . | |
| 4,834,748 | 5/1989 | McDonald . | |
| 4,895,146 | 1/1990 | Draenert . | |
| 4,997,437 | 3/1991 | Grieshaber . | |
| 5,061,238 | 10/1991 | Shuler | 606/170 X |
| 5,123,904 | 6/1992 | Shimomura et al. | 606/170 X |
| 5,152,744 | 10/1992 | Krause et al. | 606/170 X |
| 5,201,752 | 4/1993 | Brown et al. | 606/190 |

OTHER PUBLICATIONS

Gotz, Pier, Schippers, Schumpelick, Color Atlas of Laparoscopic Surgery, pp. 1–13 and 45–65.
Graber, Schultz, Pietrafitta, Hickock, Laparoscopic Abdominal Surgery, pp. 23–24 and 119–147, McGraw–Hill, Inc. 1993.
Saleh, Laparoscopy, pp. 9–41, W.B. Saunders Company 1988.
Cuschieri, Buess, and Perissat, Operative Manual of Endoscopic Surgery, pp. 209–232, Springer–verlag 1992.
Hunter and Sackier, Minimally Invasive Surgery, pp. 59–61, 157–158 and 213–229, McGraw–Hill Inc. 1993.
Ethicon Gause Dissector (Exhibit A).
Cloth Dissector (Exhibit B).

*Primary Examiner*—Michael H. Thaler
*Attorney, Agent, or Firm*—Mueller and Smith, LPA

[57] ABSTRACT

A blunt dissector instrument for laparoscopic surgical protocols is disclosed which is adapted for defining an anatomical structure from investment tissue. The dissector is formed from an elongate member which extends longitudinally between a working end and a control end, and is provided with a tip region having a blunt dissector tip and a lateral dissector region. A rough surface is circumferentially disposed about the tip portion and is effective for tactilely retaining and abrading the investment tissue for its substantially atraumatic removal from the anatomical structure.

8 Claims, 7 Drawing Sheets

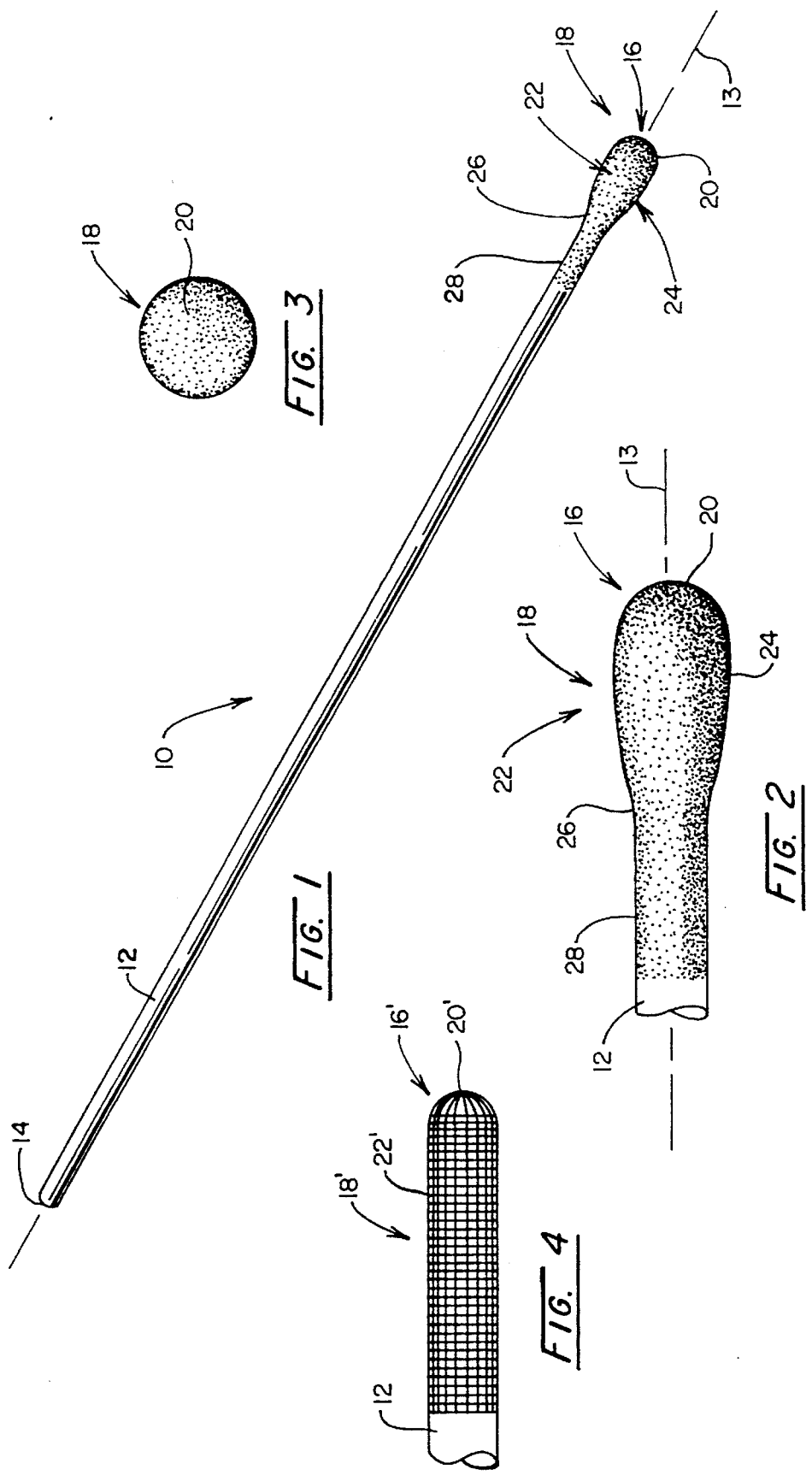

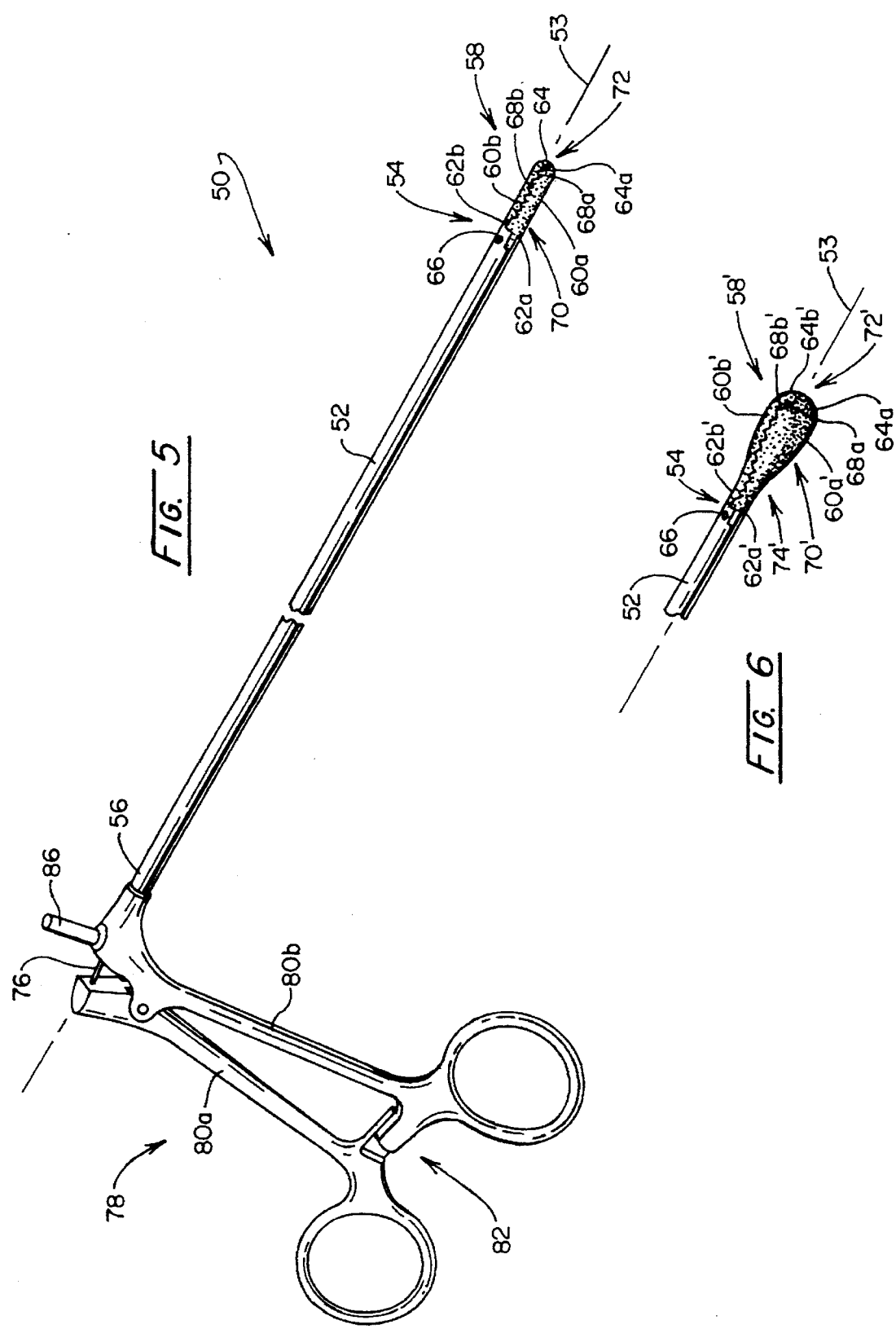

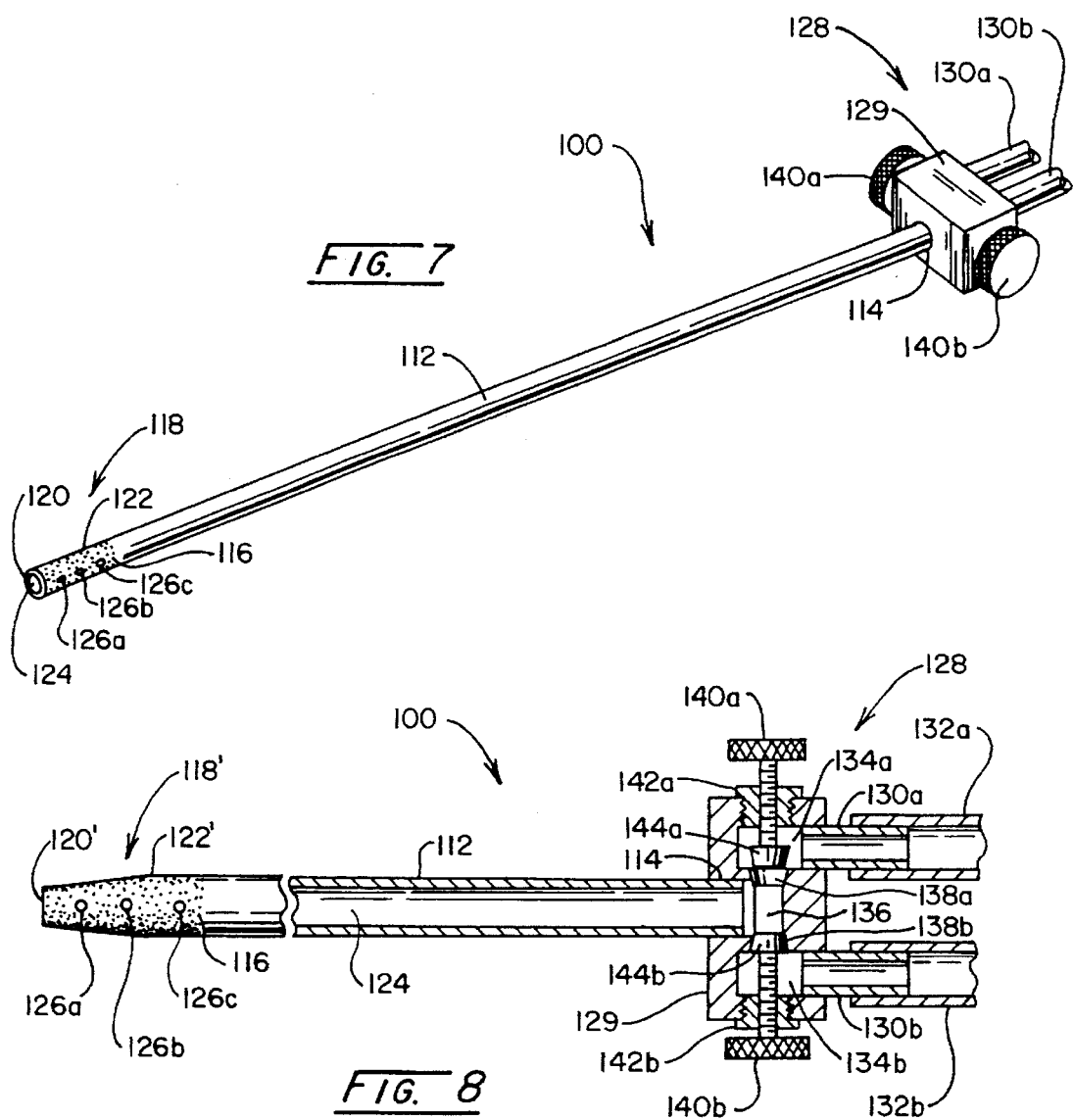

METHOD OF USING A SURGICAL DISSECTOR INSTRUMENT

CROSS-REFERENCE TO RELATED APPLICATIONS

This application is a continuation of application Ser. No. 08/168,990, filed Dec. 17, 1993 now abandoned which is a continuation-in-part of Ser No. 07/927,552 filed Aug. 6, 1992, now abandoned, which is a continuation of Ser. No. 07/610,119 filed Nov. 7, 1990, now abandoned.

BACKGROUND OF THE INVENTION

Cholecystectomy or gallbladder removal has been carried out in a structured surgical manner since about 1882. The heretofore conventional approach to the procedure has involved the surgical opening of the body cavity, typically via a right quadrant incision, and direct hand access to the organ on the part of the surgeon aided by three-dimensional vision and touch. This surgical procedure continued for over 100 years until the 1980s when a new treatment employing laparoscopy somewhat abruptly supplanted the earlier orthodox procedure. The appeal of this new treatment modality resides in the less invasive character of the procedure, which is carried out with correspondingly less pain, incision, and scar, shorter term hospitalization, and improved cost considerations.

In general, the laparoscopic approach to cholecystectomy commences with the insufflation of the peritoneal cavity of the anesthetized patient. Typically, this expansion of the cavity (pneumoperitoneum) is carried out by the controlled insertion of an insufflating agent such as carbon dioxide through a supraumbilically inserted Verres needle. That needle is operatively associated with an insufflator machine, usually providing a pressure and flow rate control over the insufflating agent. A sequence of cannulas are placed into the peritoneal cavity using sharp, removable inserts called trocars. These cannulas are valved devices through which a video imaging camera and light source along with various thin, elongate instruments can be passed and manipulated from outside of the patient's body during the procedure. Cannulas vary in port diameter, ranging, for instance, from 5 mm to 18 mm. Generally, the first cannula is installed adjacent the umbilicus and serves to initially receive a laparoscope or video camera and light source. It is the video output of this device as observed by the surgeon at a video monitor which provides all of the visual perceptive data for hand maneuvering the elongate laparoscopic instruments. As the video camera is guided by a surgical assistant, these instruments, having a necessary length of about 18 inches (45.72 cm), are held at one end by the surgeon who, while viewing the video monitor, carries out refined and delicate dissecting, isolating and clamping maneuvers within the moving, dynamic environment of the peritoneal cavity.

The gallbladder is the reservoir for bile which, with the hepatic, cystic, and common bile ducts, forms the excretory apparatus of the liver. Conical or pear shaped in gross anatomy, the gallbladder exists as a musculo-membranous sac lodged in a fossa on the undersurface of the right lobe of the liver, and extends from near the right extremity of the transverse fissure to the anterior border of the organ. It is about 4 inches (10.16 cm) in length, 1 inch (2.54 cm) in breadth at its widest part, and holds from eight to ten drachms. The organ is divided into a fundus, body, and neck or infundibulum. The fundus or broad extremity is directed downward, forward and to the right, and projects beyond the anterior border of the liver. The body and neck are directed upward and backward to the left. The vascular system of the gallbladder is derived from branches of the hepatic artery.

The upper surface of the gallbladder is attached to the liver by connective, i.e., areolar, tissue and vessels. The under surface is covered by peritoneum, which is reflected on to it from the surface of the liver. Occasionally, the whole of the organ is invested by the serosa membrane, and is then connected to the liver by a kind of mesentery. Adipose tissue often invests the gallbladder and its biliary and vascular anatomy.

In wall structure, the gallbladder consists of three coats, namely, serous, fibrous and muscular, and mucous. The external or serous coat is derived from the peritoneum and completely invests the fundus, but covers the body and neck only on their under surface. The fibro-muscular coat is a thin but strong layer which forms the framework of the sac and consists of dense, fibrous tissue which interlaces in all directions. The internal or mucous coat is loosely connected with the fibrous layer and is covered with columnar epithelium. The mucous membrane secretes an abundance of thick, viscid mucus.

As aforementioned, both the gallbladder and liver are associated with a biliary anatomy including three biliary ducts: the cystic duct, the common bile-duct (ductus communis choledochus), and the hepatic duct. The cystic duct, typically exhibiting a very small diameter of about ⅛ inch (3.175 mm) joins the hepatic duct to form a common bile duct which extends to an orifice upon the summit the papilla situated at the inner side of the descending portion of the duodenum. The external coat of the cystic duct is fibrous and composed of strong fibro-areolar tissue with a certain amount of muscular tissue arranged in a circular manner around the duct.

Because gall stones may be present in the common bile duct, under earlier, open surgical cholecystectomy procedures, the surgeon has been able to palpate the common bile duct and visualize its diameter for determining whether a cholangiogram would be necessary to detect any occult stones. This procedure was essentially straightforward utilizing the surgeon's stereoscopic direct vision and tactile senses at the fingertips. However, in laparoscopic surgery, the common bile duct is not tactilely accessible by the surgeon, but is viewed two-dimensionally and remotely on a T.V. screen, making it difficult for the surgeon to appreciate turns in the ductal structures. Thus, and as retained stones in the biliary anatomy present the possibility for injuries to the major ductal structures during laparoscopic cholecystectomy, a cholecystcholangiographic protocol is generally indicated for management of ductal stones. Indeed, cholangiography is useful both for demonstrating the cystic duct/common hepatic duct junction to delineate abnormal anatomy, and for indicating the presence of any stones in the common bile duct.

One technique for cholecystcholangiography involves retracting the gallbladder laterally and elevating it up to the abdominal wall. Upon being brought into apposition with the abdominal wall, the gallbladder is then punctured percutaneously with a needle to aspirate bile and to effect a decompression. A syringe of contrast material such as a barium fluid or the like then is attached to the needle for refilling the gallbladder with an amount of the contrast material equal in volume to the amount of bile which was aspirated. At this point, the gallbladder is viewed radiographically with a fluoroscope or the like to assess the biliary anatomy and to determine whether stones are present within the common bile duct.

Although the above-described cholangiographic technique is relatively easily effected given the constraints of two-dimensional remote vision and diminished tactile data, the injection of contrast fluid directly into the sac of the gallbladder sac engenders a risk of flushing any stones contained therein into the ductal system where removal is made more difficult. Accordingly, a cystic duct cholangiography protocol is often specified. In this protocol, the gallbladder is grasped with atraumatic grasping forceps at the fundus and, optionally, at the infundibulum to place the cystic duct in tension. Any adhesions between the gallbladder and the adjacent organs, e.g., omentum, right colon flexure and duodenum, may be bluntly divided or transected with a hooked electrode or scissors. With the gallbladder separated and adequate traction maintained, the cystic duct is dissected from its areolar and/or adipose investment using forceps, hook electrodes, or scissors. In this regard, it is generally preferred that dissection is begun at the infundibulum and proceeds in the direction of the common bile duct to expose junction of the cystic and hepatic ducts.

Upon adequate exposure of the duct, the upper neck of the gallbladder is then closed by peripherally clipping the cystic duct near its junction with the infundibulum of the gallbladder. With the gallbladder grasped near the infundibulum to stretch the cystic duct, an instrument such as a pair of laparoscopic microscissors is used to partially transect the cystic duct on the common bile duct side of the previously placed clip. Following the partial transection of the cystic duct, a cholangiography catheter is percutaneously inserted at an angle to orient the catheter towards the opening in the duct. The catheter is selected as being flexible and having outer diameter suited for insertion into the duct. The tip of the catheter is guided into the cystic duct through the opening, and is secured in the duct by clipping. It generally is preferred that saline is injected through the catheter during clipping to assure its potency. Once the catheter is secured within the cystic duct, cholangiography is performed in a routine fashion.

After satisfactory cholangiograms have been obtained, the cholecystectomy procedure continues with the retrieval of any ductal stones and, thereafter, with the division of the cystic duct. With respect to the division of the cystic duct, the duct first is clipped centrally near its junction with the common bile duct. The duct then is divided between the central clip and the peripheral clip previously placed near the infundibulum of the gallbladder. As the duct is divided, traction is maintained on the neck of the gallbladder away from the liver to more clearly expose the cystic artery.

With the cystic duct divided, the cystic artery next may be addressed. Indeed, it is preferred to first divide the cystic duct before the cystic artery is dissected as closure and division of the cystic duct as a first step permits a better identification and a safer closure of the cystic artery. As with the cystic duct, the cystic artery, for its identification, also may have to be dissected free of an areolar and/or adipose investment, again with the use of forceps, hook electrodes, or scissors. Division of the artery then may proceed via a double clip ligation and a transection with scissors between the clips.

Following the division of the cystic duct and arteries, the intraoperative procedure continues with the dissection of the gallbladder from the liver. Generally, this dissection proceeds by alternately retracting the gallbladder medially and laterally with concurrent elevation to place the interposing tissue under tension. With the interposing tissue placed in tension, it may be separated either bluntly with dissecting forceps, sharply with scissors, or with a monopolar electrosurgical instrument or a bipolar forceps. The gallbladder then may be removed from the body through a lateral trocar. For further information concerning laparoscopy and its use in conjunction with cholecystectomy, reference is made to the following publications, the disclosures of which are expressly incorporated herein by reference:

"Laparoscopy" by J. W. Saleh, W. D. Saunders Co., 1988.

"Laparoscopic Abdominal Surgery" by J. N. Graber, L. S. Schultz, J. J. Pietrafitta, and D. F. Hickok, McGraw-Hill, Inc., 1993.

"Minimally Invasive Surgery" by J. G. Hunter and J. M. Sackier, McGraw Hill, Inc., 1993.

As was mentioned, the above-described cystic duct cholangiography protocol often is specified in cholecystcholangiography to minimize the risk of stone migration from the gallbladder sac into the ductal system. Unfortunately, such protocol necessarily entails the dissection of the cystic artery from its investment prior to the taking of a cholangiogram and the identification of the biliary anatomy. The laparoscopic surgeon must therefore employ what amounts to an exploratory technique in attempting to delineate the cystic duct without causing trauma to the surrounding structures. The exploration is complicated, however, in that the surgeon must operate remotely without direct stereo vision or tactile response.

Indeed, the most common tool for the laparoscopic dissection of the cystic duct and arteries heretofore has been scissors, which are generally used in concert with forceps and retractors to effect the severance or traumatic avulsion of investment tissue. However the two-dimensional field afforded to the surgeon during laparoscopic procedures complicates the use of scissors or forceps. Such complication presents an increased risk that adjacent anatomical structures may be accidentally damaged as a result of the surgeon lacking direct stereoscopic access to the structure being dissected. Moreover, avulsive instruments such as forceps, hemostats, and tweezers inherently cause a certain amount of trauma to surrounding tissue. A not uncommon occurrence is the severance of a hepatic artery branch with the immediate result of abandonment of the laparoscopic procedure and resort to conventional open surgery.

More recently, laparoscopic surgeons have experimented with atraumatic, blunt dissecting instruments such as the Kittner or "peanut" gauze dissector. Such dissectors generally comprise an elongate 5 or 10 mm diameter rod terminating at a blunt spherical or cylindrical tip formed of a wound cotton or other fibrous material. Other of the blunt dissectors terminate in a cylindrical tip comprised of a wound, textured fabric.

Although the use of such blunt dissectors presents a lessened risk of traumatic injury to anatomical structures adjacent to the structure being dissected, the relative smoothness of the fibrous or fabric tip material precludes their use for the abrasive removal of investment tissue. The relatively low coefficient of friction of the fibrous or fabric tip material also makes the known dissectors relatively ineffective for tactilely engaging and circumferentially retaining areolar investment tissue. Thus, the use of the blunt dissectors heretofore known in the art has been limited to the dissection of structures that are loosely attached to and can be easily separated from one another via the insertion of the dissector therebetween. Additionally, the porosity and inherent structural weakness of fibrous or fabric tips necessitates that such instruments be made disposable rather than reusable. Indeed, during surgery, the fibrous or fabric tips may swell or unravel to such an extent that the instrument must be removed from the patient and replaced with a new instrument. Overall, the blunt dissectors heretofore known may be seen as less than optimally efficient and may unacceptably extend the duration of the laparoscopic procedure. It is therefore apparent that the provision of a blunt dissecting instrument which aids the laparoscopic surgeon in delineating, for example, the cystic duct and arteries would be well-received by practitioners and would represent an important improvement in laparoscopic surgery.

BRIEF DESCRIPTION OF THE DRAWINGS

FIG. 1 shows a perspective view of one embodiment of a dissector instrument in accordance with the present invention;

FIG. 2 is a fragmentary, enlarged side elevational view of the tip of the dissector instrument of FIG. 1;

FIG. 3 is an enlarged front elevational view of the tip of the dissector instrument of FIG. 1;

FIG. 4 is a fragmentary, enlarged side elevational view of the tip of a dissector instrument according to the invention and provided with a cylindrically-shaped, knurled tip;

FIG. 5 is a perspective view of another embodiment of the dissector instrument of the present invention as incorporated into a grasping-type forceps instrument;

FIG. 6 is a fragmentary perspective view of an alternative tip portion for the instrument of FIG. 5;

FIG. 7 is a perspective view of another embodiment of the dissector instrument of the present invention having a central bore extending therethrough and coupled to a manifold for fluid communication with a source of isotonic saline for irrigation and/or a vacuum source for suction;

FIG. 8 is a fragmentary, partially cross-sectional view of a dissector instrument generally in accordance with FIG. 7 showing the internal structural of the manifold shown in FIG. 7;

BROAD STATEMENT OF THE INVENTION

Figure 9:
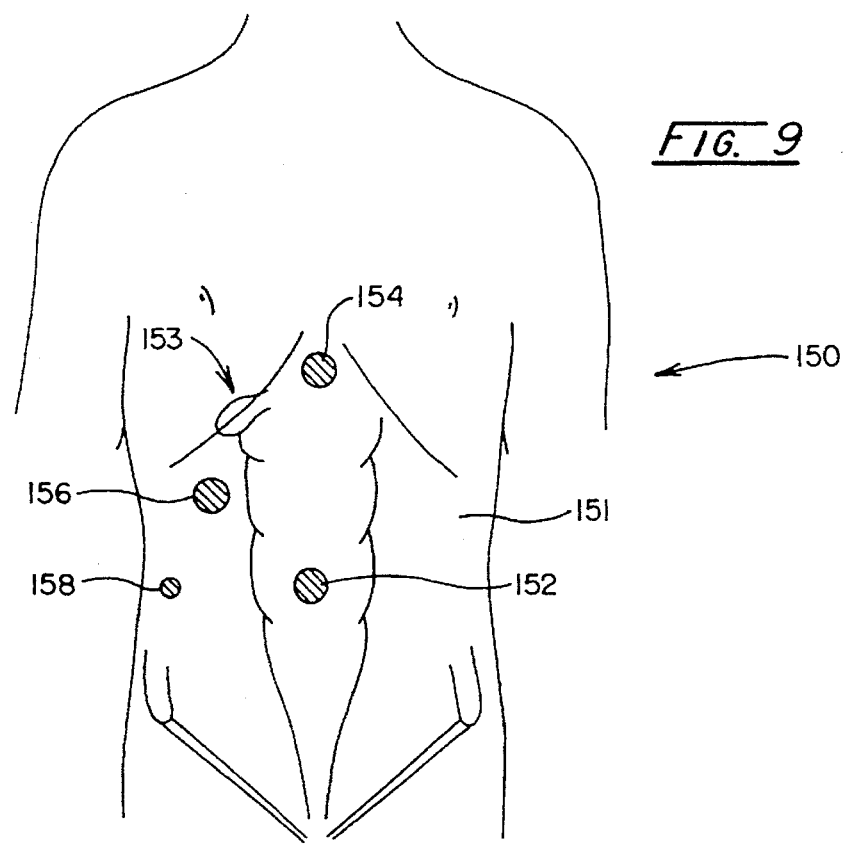
FIG. 9 is a ventral plan view of the abdomen of an insufflated patient showing the location of the cannula ports for a laparoscopic cholecystectomy or cholecystcholangiography surgical protocol.

The present invention is addressed to a blunt dissector instrument and method of use for laparoscopic surgical procedures which are especially adapted for atraumatically defining anatomical structures from investment tissue. In having an elongate member with a tip portion extending therefrom and an abrasive surface circumferentially disposed about the tip portion selected as effective for tactilely retaining and abrading investment tissue, the dissector instrument of the present invention is capable of removing even membranous tissue without unduly traumatizing the underlying anatomical structure. The instrument also is adaptable to provide suction, irrigation, and even electric current through its shaft and tip portions. Advantageously, the instrument may be incorporated into a conventional laparoscopic or endoscopic grasping-type forceps to provide a combination instrument serving the laparoscopic surgeon with increased operational flexibility.

As will be apparent, the instrument of the present invention is especially suited for use in a laparoscopic cholecystectomy or cholecystcholangiography method to define the cystic duct and the cystic artery prior to their transection. In this regard, the tip portion of the instrument of the invention may be configured to facilitate the removal of investment tissue from annularly-shaped ductal structures.

The invention, accordingly, comprises the apparatus and method possessing the construction, combination of elements, and arrangement of parts and steps which are exemplified in the following detailed description. Reference to that description and to the accompanying drawings should be had for a fuller understanding and appreciation of the nature and objects of the invention, although other objects may be obvious to those skilled in the art.

DETAILED DESCRIPTION OF THE INVENTION

The precepts of the blunt dissector instrument which is the subject of the present invention are described hereinafter in connection with its utilization in a laparoscopic cholecystectomy or cholecystcholangiography surgical protocol. However, it will be appreciated that the subject dissector will find utility in other laparoscopic surgical protocols, such as appendectomies, which involve the severance and removal of investment tissue for the delineation or dissection of anatomical structures. Indeed, the dissector of the present invention may find especial utility in obese patients whose organs commonly are invested with an abnormal amount of adipose tissue. Thus, the disclosure to follow should be construed as illustrative rather than in a limiting sense.

Referring to the figures and looking to FIG. 1, one embodiment of the dissector instrument of the invention is represented generally at 10. Instrument 10 may be seen to comprise an elongate, generally cylindrical shaft 12 which extends along a longitudinal axis 13 from a hand graspable control end 14 to a working end represented generally at 16. Working end 16 is comprised essentially of a tip region represented generally at 18 which surmounts the working end 16 and has a forward terminus 20, and extends rearwardly from terminus 20 to define a lateral dissector region 22. This lateral dissector region 22 transitions from a portion 24 of relatively larger diameter through a capture region 26 of concave cross-sectional profile to a generally linear region 28 of constant but lesser diameter than the region 24. For laparoscopic applications, it is preferred that the instrument 10, as it extends from control end 14 to the forward terminus 20 have a length from about 36 cm to about 40 cm, although the body habitus of the patient may dictate a longer length. It is preferred that the diameters exhibited by the shaft 12 as well as the tip region 18 fall within a range from about 5 mm to about 18 mm so that the instrument 10 is receivable through a standard cannula. Shaft 12 of the instrument 10 may be fabricated from a number of materials including surgical grade stainless steel such as a 316-type or equivalent, anodized aluminum, or an extruded or pultruded polymeric material or composite. In general, the surgeon will hand manipulate instrument 10 by grasping it at control end 14. Such manipulation will involve the movement of the instrument in a motion which is coplanar with longitudinal axis 13 and/or rotational about axis 13. Additionally, a lateral movement backwards and forwards along axis 13 occurs generally during the manipulation of the instrument 10 to a cannula and to the situs of the dissection.

Looking additionally to FIG. 2, the tip region 18 is illustrated in somewhat enhanced detail. This tip portion 18 is provided with a rough surface and the profile of the lateral dissector region 22 is seen to be gently curved at portion 24 as it transitions from the forward terminus 20 rearwardly. Region 22 then transitions through a concave profile defining capture region 26 to a region of linear profile 28. The diameter exhibited by lateral dissector region 22 at the rearward portion 28 is smaller than the corresponding diameter at region 24. Region 22 functions to engage and remove investment tissue from anatomical structures by both rotation of instrument 10 about axis 13 and movement of the instrument coplanarly with axis 13.

FIG. 3 shows the blunt forward dissector region at forward terminus 20. This blunt forward dissector region at 20 is seen in FIG. 2 to be convexly curved to effect a dissecting function principally when the instrument 10 is moved coplanarly with axis 13 but also during rotation about that axis. The smooth curvature of the tip region 18 as described above in connection with FIG. 2 exhibiting a gradually increasing and then decreasing diametric extent functions to faciliate the removal of instrument 10 from a cannula within which it may have been inserted and the shoulders or other protrusions which might otherwise snag in the cannula or on its openings are minimized. A further advantage gained from the preferred tip region 18 profile represented in FIGS. 1–3 is the larger diametric extent of the lateral dissector region 24 which exhibits additional surface area to enhance and increase tissue contact. Additionally, when the instrument 10 is rotated during the dissecting procedures about axis 13, the surface speed of region 24 is correspondingly increased to afford some amplification of the maneuver carried out by the surgeon.

The concave capture region 26 of the lateral dissector region 22 has been observed to facilitate the dissection or removal of investment tissue from ductal structures. It may be recalled that the surgeon is constrained to two-dimensional observation of the dissection procedure during laparoscopic surgery, being limited to the remote view at a video screen. The capture region 24 functions to gently engage the structure of annular ducts such as the cystic duct and the cystic artery. Once such ducts are engaged, the instrument 10 may be manipulated coplanarly as well as rotationally with respect to axis 13 along the ducts to remove investment tissue without damaging the duct structures. While this procedure is occurring, the duct structures will flex slightly as seen on the video screen by the surgeon, and thus the surgeon will have information or visual data representing the otherwise unobservable third-dimension vision. Note, additionally, that during this delicate and highly important procedure, the damage which might otherwise be caused by a sharp tip or the like is avoided because of the profile of the blunt forward dissector region 20. In general, it is desirable that the lateral dissector region 22 have a length of between about 10 mm and 20 mm.

Considering next the structural and functional attributes of the rough surface at tip region 18, it is generally preferred that surface 22 be provided as a particulated or film coating formed of a superabrasive or like material. In this sense, it will be understood that suitable superabrasive materials include natural diamond or synthetic high or low pressure diamond, amorphous or diamondlike carbon films, crystalline carbon, boron nitrides such as cubic boron nitrides, and silicon carbides, as well as ceramics. Such materials may be adhesively bonded to the tip region 18 substrate, or the materials may be plated to the substrate using, for example, a nickel electroplating solution. Alternatively, the materials may be brazed to the substrate or deposited thereon using chemical vapor deposition techniques. In general, the non-yielding, roughened surfaces of lateral dissector region 22 and blunt forward dissector region 20 are provided to be of a roughness effective to tearably engage and remove investment tissue while remaining in physical, non-distinctive contact with adjacent anatomical structures such as the cystic duct or artery.

Looking to FIG. 4, an alternative arrangement is illustrated wherein tip region 18, as is represented in the figure at 18', is presented as having a cylindrically-shaped lateral dissector region 22 with an outer constant diameter substantially the same as that of shaft 12. As also may be seen by reference to FIG. 4, the roughened surface of the tip region 18' may be provided as a knurled surface machined into tip region 18 or 18'. In this regard, it has been found that a ¹⁄₁₆ inch (1.4 mm) diametrical pitch knural is preferred. As is shown in FIG. 4, the knurled surface may be provided to extend over the convex surface of the forward terminus of the instrument to form the blunt forward dissector region.

As to its preferred surface morphological characteristics, the roughened surface generally is provided as having grit or mesh size of about 80 to 100 corresponding to a nominal particle size of from about 0.0059 inch (1.5875 mm) to about 0.007 inch (0.1778 mm). It has been found that such a grit or mesh size is effective, with respect to areolar or adipose investment tissue, to engage and tear away or to tactilely retain, i.e., to hold or wrap circumferentially about tip portion 18, such tissue without causing undue avulsive or other trauma to the anatomical structure undergoing dissection. In this regard, diamond or other superabrasive coatings are especially preferred as having particle sizes which may be tailored to the operational needs of the surgeon.

Preferably, tip portion 18 is integrally fabricated from the same material of construction as that of shaft member 12, and is used as the substrate on which the roughened surface is bonded, plated, deposited, or otherwise coated. Alternatively, however, tip portion 18 may be separately fabricated and made interchangeable via, for example, a threaded engagement with shaft 12, or it may be permanently joined, welded, or bonded to shaft member 12. For example, shaft member 12 may be fabricated from an anodized aluminum tube or rod with tip portion 18 fabricated from a 316-type stainless steel or equivalent. In forming elongate shaft member 12, tip portion 18 or 18', and/or abrasive surface 22 or 22' from electrically conductive materials or coatings, an instrument 10 may be developed as having a surface or bulk conductivity making it couplable to a power supply for providing a current output at tip portion 18 or 18'. When so coupled, instrument 10 is adapted for use as both a blunt dissector and as a monopolar electrosurgical scalpel.

Looking next to FIG. 5, a second embodiment of the dissector instrument of the present invention is shown generally at 50 as incorporating a grasping-type forceps. Although grasping-type forceps, such as commercially-available biliary duct or endoscopic forceps of the types shown in Hunter and Sackier, p. 157–158, and in graber and Schultz, pp. 23–24, are commonly employed in laparoscopic surgical procedures for retracting tissue, certain circumstances dictate their withdrawal from the patient for replacement with an instrument more adapted for dissecting tissue. In this regard, instrument 50 affords the laparoscopic surgeon the advantages of both a dissector and a forceps without having to withdraw and exchange instruments.

Instrument 50 may be seen to comprise a generally elongate shaft 52, extending along an axis 53 between a first end, 54, and a second end, 56. As is represented generally at 58, a pair of jaws, 60a and 60b; each having a connecting end, 62a and 62b, and each extending to a tip, 64a and 64b, are positioned at first end 54 of shaft member 52 for forming a tip portion. Jaws 60a and 60b are mutually pivotally coupled by a pivot pin 66 connecting ends 62a and 62b for movement between an open and a closed orientation. In conventional fashion, each of the jaws 60a and 60b is formed having an inwardly facing, toothed engaging surface as represented at 68a and 68b which are formed in complementary fashion to effect an interlocking form of abuttable joining when the jaws are in their fully closed orientation as shown in the figure. The outward surface of each jaw 60a and 60b is roughened in the same manner as the earlier embodiment of FIGS. 1–3 or FIG. 4. As such, the outwardly disposed surfaces of the jaw pair 58 form a dissector instrument forward portion having a lateral dissector region 70 formed of two partial lateral dissector regions, one associated with the outward surface of each jaw 60a and 60b. This lateral dissector region 70 extends to a tip formed of the forwardly disposed tips 64a and 64b and which combine to define a blunt forward dissector region represented at 72. The rough surface of lateral dissection region 70 and blunt forward dissection region 72 are provided in the manner described in conjunction with FIGS. 1–3 or FIG. 4 and are selected such that the rough surface is effective to tearingly engage and remove the investment tissue while remaining in physical, non-destructive contact with adjacent anatomical structure such as a cystic duct or cystic artery. The formation of such surface is made so as to be effective for tactilely, transiently engaging, retaining, and removing investment tissue in the process of defining anatomical structures without harming such anatomical structures, i.e. providing for the atraumatic removal of investment tissue. The rough surfaces may be provided as particulated or film coatings formed of a superabrasive or like material, or may be developed by machining to provide, for example, a knurled form of surface as seen in FIG. 4.

Looking to FIG. 6, an embodiment for the jaws of the instrument 50 emulating the desirable dissector structuring described in conjunction with FIGS. 1–3 is illustrated. The jaw pair is represented generally at 58' to include two jaws 60a' and 60b' having connector ends at 62a' and 62b' which are pivotally coupled to the shaft 52 at pin 66. The jaws 60a' and 60b' extend from their pivotal connection at 66 to tips 64a' and 64b', each of which serves to form a partial forward dissector region. The regions between tips 64' serve to form lateral dissector regions Jaws 60a' and 60b' are configured having mutually inwardly facing toothed engaging surfaces 68a' and 68b' which are in interlocking abutment when the jaw structure 58' is in its closed orientation is shown. In that same orientation as shown, the instrument 50 becomes a dissector having a lateral dissector region 70' and a blunt forward dissector region 72'. Additionally as in the case of the embodiment of FIGS. 1–3, a portion of concave profile within the lateral dissector region 70' serves as a capture region 74'.

Returning to FIG. 5, a drive member, 76, is coupled in a drive relationship with connecting ends 62a and 62b of jaws 60a and 60b for movement between their open and closed orientations. An actuator assembly, shown generally at 78, and which may be of a manually-actuable scissors-type arrangement including a pair of looped handles, 80a and 80b, is coupled with drive member 76 for actuating it to move jaws 60 between their open and closed orientations. Preferably, as is shown at 82, handles 80 are configured to effect a mechanical interlocking engagement therebetween to lock jaws 60 in their closed orientation. Alternatively, a trigger-type assembly (not shown) may be provided for locking jaws 60a and 60b in their closed orientation.

For adapting instrument 50 for use additionally as a monopolar electrosurgical scalpel, an electrode pin, 86, may be provided for making instrument 50 couplable to a power supply providing a current output at jaw pair end 58 or 58'. Alternatively, two electrode pins (not shown) may be provided for configuring instrument 50 as a bipolar electrosurgical scalpel. In this configuration, each of jaws 60a and 60b, when maintained in their opened orientation, function as separate electrical poles, i.e., an active electrode and a grounding electrode, to confine the current flow therebetween. In this regard, bipolar instruments are often preferred for surgical applications as being less prone to current leakage, capacitive coupling, or accidental discharges.

Turning to FIG. 7, shown generally at 100 is another embodiment of the dissector instrument of the present invention as adapted to be fluid communicable with a source of isotonic saline for irrigation or a vacuum source for suction. In this embodiment, instrument 100 is again comprised of an elongate, generally annular shaft member, 112, extending longitudinally between a first end, 114, and a second end, 116. A cylindrically-shaped tip portion, shown generally at 118, is provided to extend between a tip, 120, and end 116 of elongate shaft 112. Tip portion 118 has a rough surface, 122, which may be provided as a particulated or film coating formed of a superabrasive or like material, or as a knurled surface as described previously.

For adapting instrument 100 to be fluid communicable with a source of suction or irrigation, shaft member 112 is provided throughout its length with a central conduit or cavity, represented at 124, extending longitudinally through tip portion 118 and opening into tip 120. Optionally, additional suction or irrigation ports or fenestrations may be provided along tip portion 118 as are represented at 126a–c. Looking additionally to FIG. 8, wherein, as is represented at 118', tip portion 118 of instrument 100 is shown as being generally conically-shaped, it may be seen that first end 114 of shaft member 112 is fluidly coupled to a manifold assembly, represented generally at 128. Assembly 128 may be actuated for controlling the flow of fluids in irrigation and suction modes. Manifold 128 has a housing, 129, and a pair of ports, 130a and 130b, leading thereinto which couple to a pair of corresponding lines, 132a and 132b, leading to, respectively, irrigation and suction sources. Ports 130a and 130b fluidly couple corresponding lines 132a and 132b to central bore 124 via a pair of corresponding chambers, represented at 134a and 134b, which lead into a central chamber, represented at 136, through a pair of adjoining orifices, represented at 138a and 138b. For controlling the fluid flow through central chamber 136, a pair of stopcocks, 140a and 140b, are provided to be threadably engageable with a corresponding pair of threaded inserts, 142a and 142b. Stopcocks 140 are rotatably adjustably positionable through chambers 134, and each have a seating portion, 144a and 144b, configured to be received by a corresponding orifice 138 to thereby affect the flow of fluid through central chamber 136. In this manner, suction or irrigation through instrument 100 may be alternatingly actuated and controlled to assist the surgeon in removing tissue from the anatomical structure undergoing dissection.

Referring next to the sequence of FIGS. 9–16, the methodology of the present invention is illustrated in connection with the utilization of dissector instrument 10 in a laparoscopic cholecystectomy or cholecystcholangiography surgical protocol. However, it will be understood that the dissector instruments of the invention may be readily utilized for other procedures such as laparoscopic appendectomies.

Looking first to FIG. 9, the ventral view of an insufflated patient is shown generally at 150 as positioned for intra-abdominal access to the peritoneal cavity, 151. A number of representative cannular ports are depicted, including an umbilical port, 152, an epigastric port, 154, a mid-clavicular port, 156, and an anterior auxiliary port, 158. Umbilical port 152, epigastric port 154, and mid-clavicular port 156 may be provided as having 10 mm port diameters while anterior auxiliary port 158 may be provided as having a 5 mm port diameter. However, the number, the port diameter size, and even the location of the cannulas used to access the location of the gaul bladder, represented at 153, may vary depending on such factors as the body habitus of the patient and the internal structure of the biliary anatomy.

Figure 10:
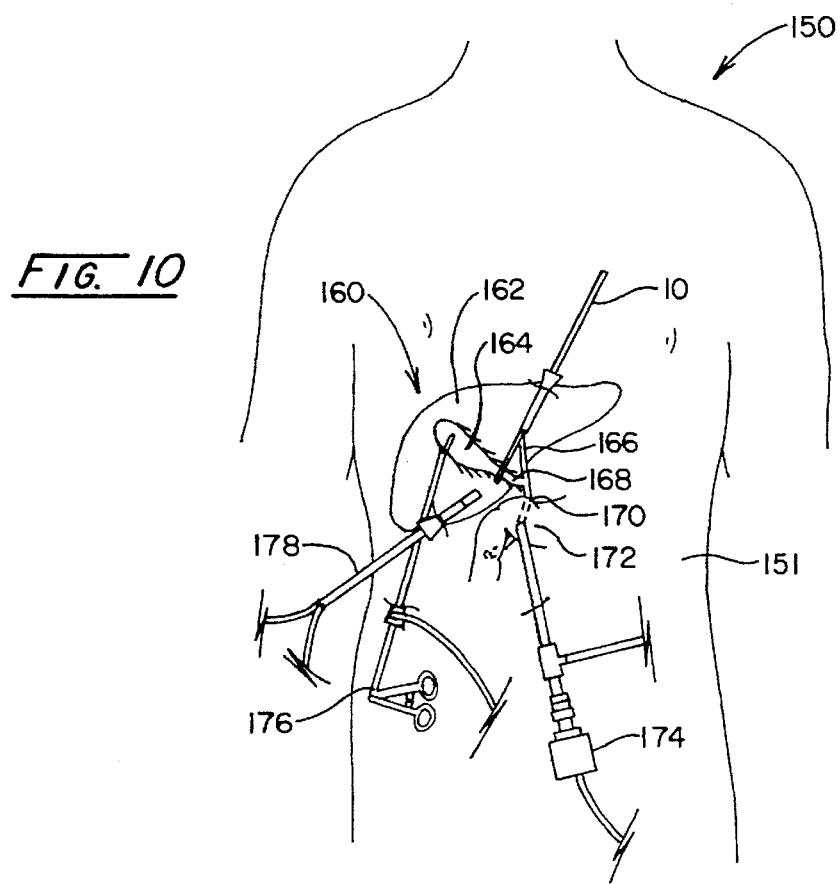
FIG. 10 is a ventral plan view of the patient of FIG. 9 showing the internal biliary anatomy of the peritoneal cavity including the gallbladder and cystic duct, and also showing the cannula ports as holding an arrangement of laparoscopic instruments including the blunt dissector instrument of FIG. 1.

Looking next to FIG. 10, cavity 151 is shown as having inserted thereinto a number of representative laparoscopic surgical instruments passed through ports 152, 154, 156, and 158, and into visual or tactile contact with the internal biliary anatomy, represented schematically at 160, of patient 150. In this regard, biliary anatomy 160 may be seen to include the liver, 162, an attached gallbladder, 164, and a ductal system comprised of a hepatic duct, 166, and a cystic duct, 168, leading from, respectively, liver 162 and gallbladder 164, and junctioning to form a common bile duct, 170, leading into the duodenum, 172. As is commonly practiced, although, again, the exact arrangement may vary, ports 160, 162, and 164 receive, respectively, a laparoscope or video camera, 174, a grasping-type forceps, 176, and a suction and/or irrigation tube, 178. In accordance with the present invention, epigastric port 154 receives dissector instrument 10, although instruments 50 and 100 may be substituted or used additionally in conjunction with instrument 10.

Figure 11:
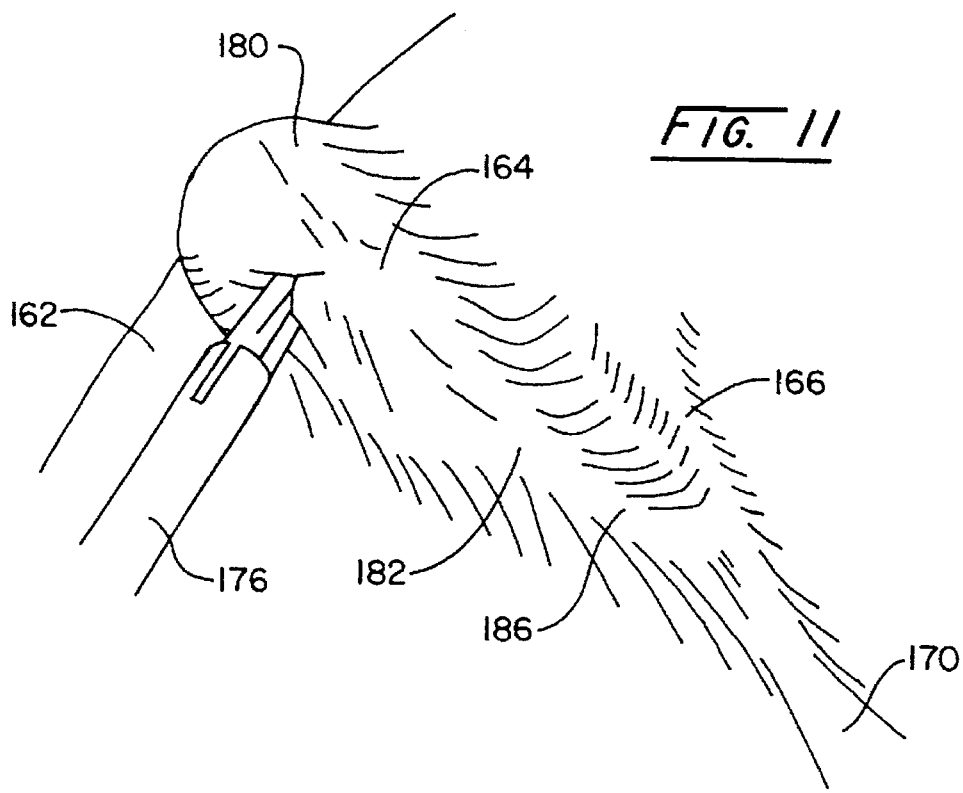
FIG. 11 is an enlarged perspective view portraying the internal view of laparoscopic cholecystectomy or cholecystcholangiography surgical procedure wherein the gallbladder is intra-abdominally retracted to place the cystic duct in tension.
Figure 12:
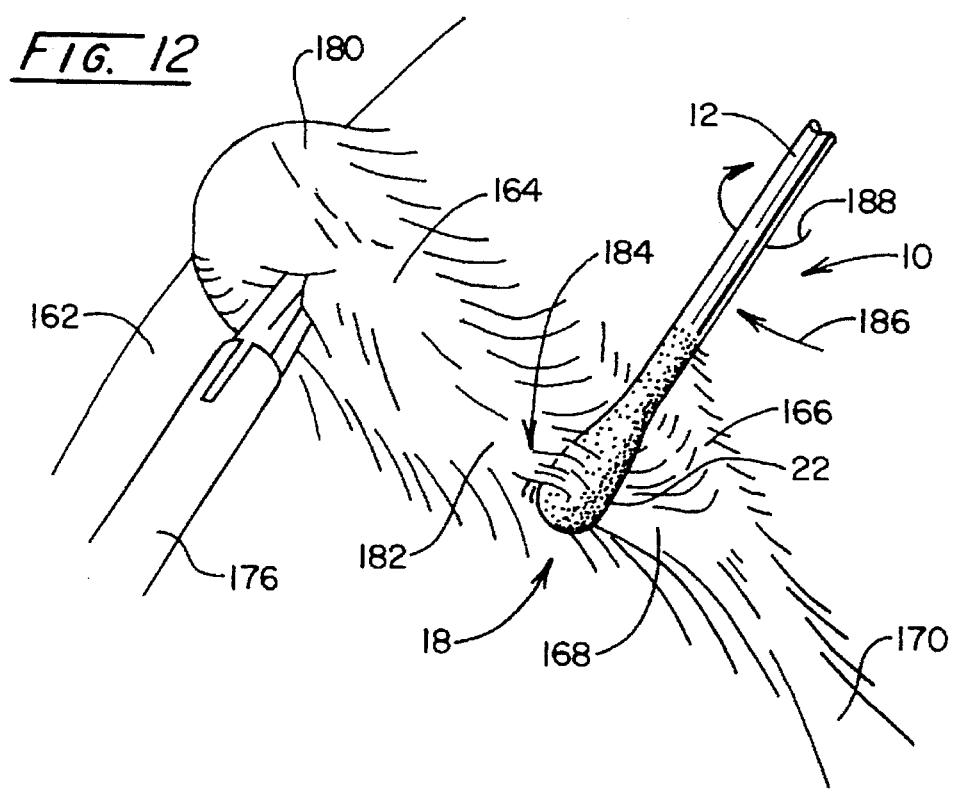
FIG. 12 is an enlarged perspective view of the continuing laparoscopic surgical procedure of FIG. 11 showing, in accordance with the precepts of the present invention, the use of the dissector instrument of FIG. 1 to remove investment tissue covering the cystic duct.

Turning to FIG. 11, wherein biliary anatomy 160 is shown in enhanced detail, the laparoscopic cholecystectomy or cholecystcholangiography procedure utilizing the present invention commences with the grasping with grasping forceps 176 of the fundus, 180, of gallbladder 164, and the medial retraction thereof to place cystic duct 168 in tension. Optionally, the infundibulum, 182, of gallbladder 164 also may be grasped and mobilized with a second pair of grasping forceps. Proceeding to FIG. 12, with traction maintained on gallbladder 10, instrument 10 is introduced at the epigastric port 154 to dissect cystic duct 168 from its investment tissue, represented at 184. For purposes of the present invention, it will be appreciated that investment tissue 184 may comprise areolar, mesentery, adhesive, connective, or peritoneum membranous tissue or attachments, as well as adipose tissue. In separating cystic duct 168 from its investment, shaft 12 of instrument 10 may be laterally reciprocated, as is represented by arrow 186, to develop a corresponding lateral motion of tip region 18. Alternatively, depending upon the physical properties of tissue 184; e.g., tensile strength, elasticity, etc., shaft 12 of instrument 10 may be rotated, as is represented by arrow 188, to develop a corresponding rotational motion of tip region 18.

Depending upon the mode of operation and whether the tissue addressed is membranous or adipose, the particular surface characteristics, e.g., hardness, coefficient of friction, etc., of the rough surface at tip region 18 make it effective to engage and draw away or abrade by minute tearing action the investment tissue 184. That is, the rough surface works to separate investment tissue 184 from, for example, cystic duct 168 via either an abrasive separation somewhat analogous to scraping wherein the tissue is in some degree particulated and removed, or via a tactile engaging retention or teasing separation wherein the tissue is retained or wound about the periphery of tip 18 allowing the tissue to be pulled from the anatomical structure. However, the surface characteristics of the rough surface provided on lateral dissector region 22 also are selected such that the underlying structure is not substantially damaged upon contact therewith. Thus, in this respect, instrument 10 may be seen as effecting a substantially atraumatic dissection notwithstanding that unintended or other contact may be made with those anatomical structures which are required to remain intact or secure such as arteries, i.e. the cystic artery and, of course, the cystic duct, the subject of the dissection itself. Inadvertent severance of the cystic artery typically calls for immediately aborting the laparoscopic technique and reverting to open surgery. Thus, the feature of the present instrument permitting the removal of investment tissue while actually contacting or rubbing biliary ducts and arteries such as the cystic artery become quite important. Effective isolation of the cystic duct and artery can be accomplished under the sight and tactile constraints of laparoscopic surgery while substantially minimizing the risk of arterial or duct rupture. This feature calls for the selection of a grit-deposited or equivalent surface configuration for lateral dissector region 22 which is effective to remove investment material while the contact of the surface with anatomical duct or arterial components does not adversely affect their integrity.

Figure 13:
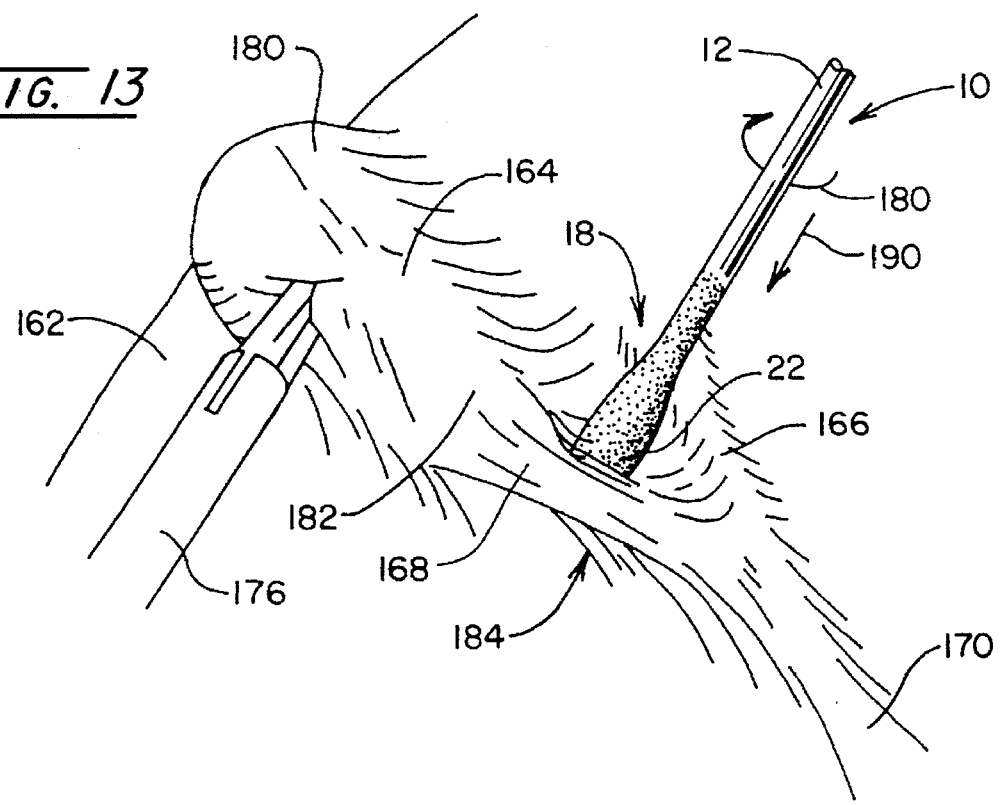
FIG. 13 is an enlarged perspective view of the continuing laparoscopic surgical procedure of FIG. 12 showing the use of the dissector instrument of FIG. 1 to effect an initial separation of the backside of the cystic duct from its investment tissue.
Figure 14:
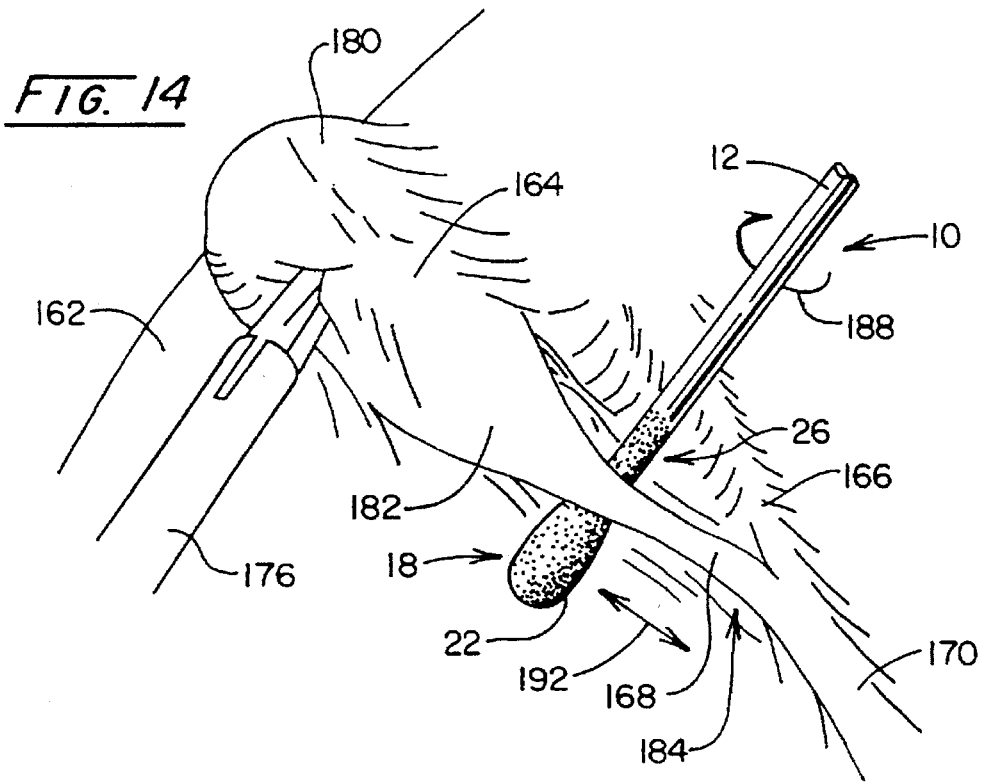
FIG. 14 is an enlarged perspective view of the continuing laparoscopic surgical procedure of FIG. 13 showing the further use of the dissector instrument of FIG. 1 to complete the dissection of the cystic duct from its investment tissue.

Looking next to FIGS. 13 and 14, the procedure continues with the further delineation of cystic duct 168 from investment tissue 184. In FIG. 13, a third modality of operation for instrument 10 is illustrated. As is represent by arrow 190, shaft 12 may be medially reciprocated upon the insertion of tip 18 behind cystic duct 168. To assist in the insertion, terminus tip 20 (hidden from view) of tip portion 18 may be employed, via the rotation of shaft 12 as represent again by arrow 188, to bore through investment tissue 184 and thereby effect an initial separation of cystic duct 168. As is shown in FIG. 14, once an initial separation of cystic duct 168 from investment tissue 184 is effected, shaft abrasive surface 26 and tip portion 18 capture region 26 (hidden from view) are especially adapted to delineate the backside of cystic duct 168 via, for example, the rotation of shaft 12 as again is represent by arrow 188 and/or its lateral reciprocation to effect a corresponding reciprocation of tip portion 18 as is represent by arrow 192. It may be recalled that the vision of the surgeon during laparoscopic surgery is limited to the two dimensions available at a remote video screen. The manipulations represented by FIGS. 13 and 14 show a capability for slightly moving the cystic duct. This permits a two dimensional verification or visual data feedback of the location (medial) of the tip region 18.

Figure 15:
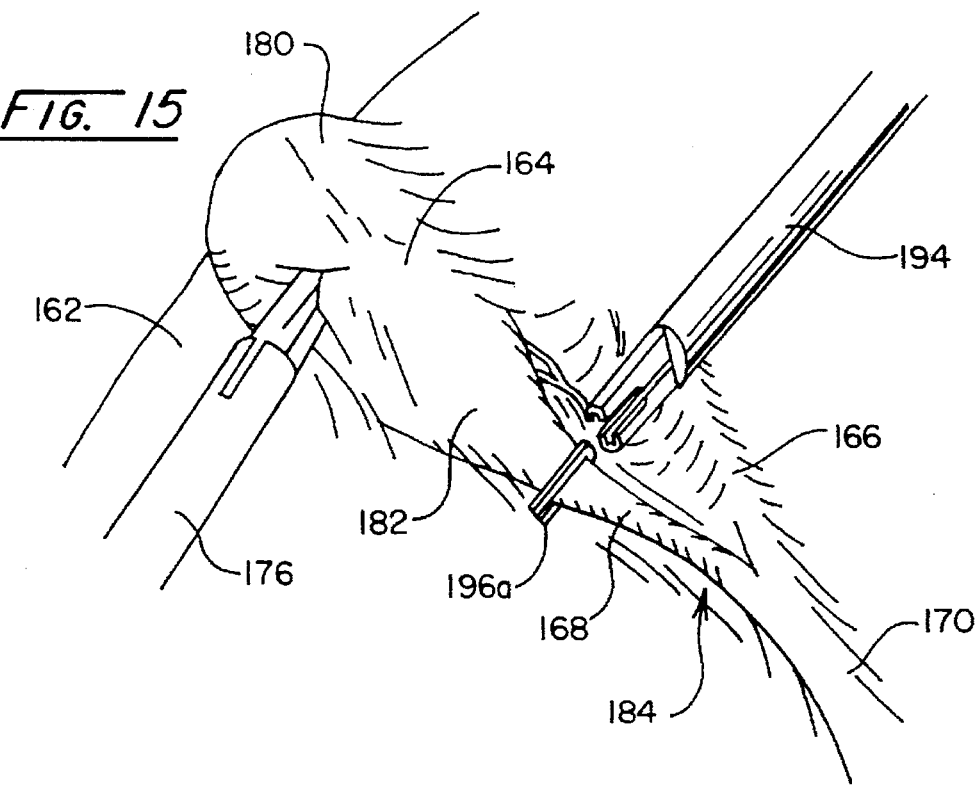
FIG. 15 is an enlarged perspective view of the continuing laparoscopic surgical procedure of FIG. 14 showing, preparatory to the transection of the cystic duct, the closing of the infundibulum of the gall bladder via the application of a surgical clip to an adjoining portion of the cystic duct.

Continuing to FIG. 15, upon the adequate exposure of cystic duct 168, the upper neck of gallbladder 164 may be closed by peripherally closing cystic duct 168 near its junction with infundibulum 168. Such closure may be effected using a commercial clip applicator, 194, to apply a surgical clip, 196, to cystic duct 168. At this point, with infundibulum 168 of gallbladder 164 closed, an exploration of common bile duct 170 optionally may be undertaken using cholangiography procedures to detect the presence of any ductal stones. The detected stones may be removed using conventional retrieval techniques. After satisfactory cholangiograms have been obtained and following the extraction of any ductal stones, additional clips, 196a and 196b (FIG. 16), are applied to cystic duct 168 near its junction with common bile duct 170 and hepatic duct 166. Cystic duct 168 then is divided between clip 196a and clip 196b.

Figure 16:
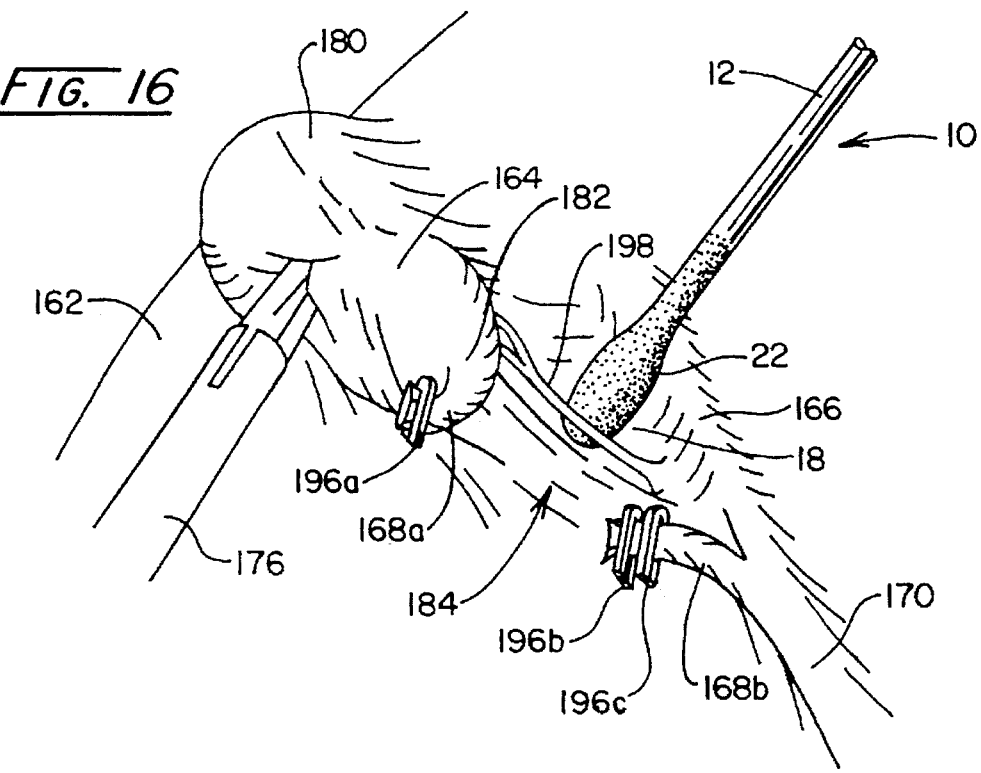
FIG. 16 is an enlarged perspective view of the continuing laparoscopic surgical procedure of FIG. 15 showing the use of the dissector instrument of FIG. 1 to delineate the cystic artery prior to its transection.

Lastly, as shown in FIG. 16, with cystic duct 168 transection into duct portions 168a and 168b, traction is maintained on gallbladder 164 to expose the cystic artery, 198. As with cystic duct 168, cystic artery 198 is dissected free of investment tissue 184 for identification. Again, instrument 10 is employed in the manner described in connection with the dissection of cystic duct 168. Once dissected, cystic artery 168 may be divided using a double clip ligation procedure similar to that described for the transection of cystic duct 168. Following the dissection of gallbladder 164 from liver 162, the cholecystectomy then concludes with the extraction of gallbladder 164 from peritoneal cavity 151 (FIG. 1) through one of lateral ports 156 or 158.

As it is anticipated that certain changes may be made in the present invention without departing from the precepts herein involved, it is intended that all matter contained in the foregoing description shall be interpreted as illustrative and not in a limiting sense.

What is claimed:

1. For a laparoscopic surgical protocol in an insufflated patient having peritoneal cavity access cannulas, a method of defining anatomical structure including fluid conveying duct and artery structures from invest tissue comprising the steps of:
    (a) providing a dissector instrument comprising:
        (i) an elongate shaft member extending along longitudinal axis between a hand-graspable control end and a working end;
        (ii) a tip portion of circular cross section transverse to said at said working end, having a surface with a blunt forward terminus of curved profile said axis and extending therefrom along said axis to provide a lateral dissector region having a concavely curved profile defining a capture region of lesser sectional extent and transitioning therefrom to a rearward portion;
        (iii) a non-yielding abrasive surface circumferentially disposed said tip portion having a roughness effective to engage and draw away investment tissue by minute tearing action while remaining in physical, destructive contact with said duct and artery structures;
        (iv) said control end being configured generally cylindrically for grasping to effect lateral movement of said tip in coplanar relationship with said and to effect hand grasp derived rotational movement about said axis;
    (b) inserting said dissector instrument into the peritoneal cavity of said patient through one of said access cannulas;
    (c) placing said tip portion of said dissector instrument in contact with said investment tissue;
    (d) hand manipulating said dissector instrument at said control end to reciprocate said tip portion along said axis in contact with said investment tissue to effect removal thereof by said minute tearing action, to engage a said duct structure at said captive region and laterally reciprocate said tip in coplanar relationship with said axis to effect atraumatic removal of said investment tissue associated therewith, to engage a said artery structure at said captive region and laterally reciprocate said tip in coplanar relationship with said axis to effect atraumatic removal of said investment tissue, and to rotate said tip about said axis while said lateral dissector region is in contact with said investment tissue to effect removal of said investment tissue by said minute tearing action; and
    (e) selectively repeating step (d) until said anatomical structure is differentiated from said investment tissue.

2. The method of claim 1 wherein said rough surface of said instrument comprises one or more of a superabrasive polycrystalline particle or polycrystalline film coating.

3. The method of claim 2 wherein said coating is formed from one or more of the following materials: a diamond, an amorphous carbon, a crystalline carbon, a boron nitride, a silicon carbide, or a ceramic.

4. The method of claim 3 wherein said coating has a grit or mesh size of from about 80 to about 100.

5. The method of claim 1 wherein said rough surface of said instrument is knurled.

6. The method of claim 5 wherein the knurling of said rough surface has a grit size of about 100.

7. The method of claim 6 wherein said knurling has a diametrical pitch of about ¹⁄₁₆ inch (1.5875 mm).

8. The method of claim 1 wherein said anatomical structure includes the cystic duct and cystic artery.

* * * * *